US008946208B2

(12) United States Patent
Castile et al.

(10) Patent No.: US 8,946,208 B2
(45) Date of Patent: Feb. 3, 2015

(54) NON-AQUEOUS PHARMACEUTICAL COMPOSITION

(75) Inventors: Jonathan Castile, Nottingham (GB); Alan Smith, Nottingham (GB); Yu-Hui Cheng, Nottingham (GB); Peter James Watts, Nottingham (GB)

(73) Assignee: Archimedes Development Limited, Nottingham (GB)

( * ) Notice: Subject to any disclaimer, the term of this patent is extended or adjusted under 35 U.S.C. 154(b) by 220 days.

(21) Appl. No.: 12/201,226

(22) Filed: Aug. 29, 2008

(65) Prior Publication Data
US 2009/0233912 A1 Sep. 17, 2009

(30) Foreign Application Priority Data

Aug. 31, 2007 (EP) .................................. 07253433
Sep. 20, 2007 (GB) .................................. 0718318.9

(51) Int. Cl.
*A01N 43/62* (2006.01)
*A61K 31/55* (2006.01)
*C07D 243/12* (2006.01)
*A61K 9/00* (2006.01)
*A61K 9/08* (2006.01)
*A61K 31/5517* (2006.01)
*A61K 47/10* (2006.01)
*A61K 47/14* (2006.01)
*A61K 47/22* (2006.01)

(52) U.S. Cl.
CPC ................. *A61K 9/0043* (2013.01); *A61K 9/08* (2013.01); *A61K 31/55* (2013.01); *A61K 31/5517* (2013.01); *A61K 47/10* (2013.01); *A61K 47/14* (2013.01); *A61K 47/22* (2013.01)
USPC ............................ 514/221; 514/220; 540/504

(58) Field of Classification Search
USPC ................... 514/220, 221; 540/504
See application file for complete search history.

(56) References Cited

U.S. PATENT DOCUMENTS

| | | | |
|---|---|---|---|
| 4,863,720 A | 9/1989 | Burghart et al. | |
| 4,950,664 A | 8/1990 | Goldberg | |
| 5,428,006 A | 6/1995 | Bechgaard et al. | |
| 5,589,475 A | 12/1996 | Snorrason et al. | |
| 5,693,608 A | 12/1997 | Bechgaard et al. | |
| 6,063,394 A | 5/2000 | Grosse-Bley et al. | |
| 6,610,271 B2 | 8/2003 | Wermeling | |
| 6,627,211 B1 | 9/2003 | Choi et al. | |
| 6,767,533 B1* | 7/2004 | Casellas et al. ............... | 424/59 |
| 2002/0032171 A1 | 3/2002 | Chen et al. | |
| 2002/0082307 A1* | 6/2002 | Dobrozsi et al. ............ | 514/772 |
| 2003/0180364 A1 | 9/2003 | Chen et al. | |
| 2003/0211123 A1 | 11/2003 | Shukla et al. | |
| 2004/0077540 A1 | 4/2004 | Quay | |
| 2004/0176359 A1 | 9/2004 | Wermeling | |
| 2005/0287181 A1* | 12/2005 | Murthy ............................ | 424/400 |
| 2006/0210604 A1 | 9/2006 | Dadey et al. | |
| 2007/0071687 A1 | 3/2007 | Wermeling | |
| 2008/0070904 A1 | 3/2008 | Jamieson et al. | |
| 2008/0279784 A1 | 11/2008 | Cartt et al. | |

FOREIGN PATENT DOCUMENTS

| | | |
|---|---|---|
| EP | 1 374 855 A1 | 1/2004 |
| JP | 08-333244 A | 12/1996 |
| WO | 01/06987 A2 | 2/2001 |
| WO | 2005/067893 A2 | 7/2005 |
| WO | 2005117830 A1 | 12/2005 |
| WO | 2006/041942 A2 | 4/2006 |
| WO | 2006/122217 A2 | 11/2006 |
| WO | 2007056424 A2 | 5/2007 |
| WO | 2008027357 A2 | 3/2008 |
| WO | 2009/046444 A2 | 4/2009 |

OTHER PUBLICATIONS

Martindale: "The Complete Drug Reference", 1999, Pharmaceutical Press, 32nd. Ed., pp. 635-639.
A. Gringauz, "Introduction to Medicinal Chemistry: How Drugs Act and Why", 1997, pp. 578-586.
Goodman & Gilman's, "The Pharmacological Basis of Therapeutics", 9th Ed., McGraw Hill, 1996, p. 383.
S. Bjorkman et al., "Pharmacokinetics of midazolam given as an intranasal spray to adult surgical patients", British Journal of Anaesthesia, 1997; 79: pp. 575-580.
Niall C. T. Wilton, et al., "Preanesthetic Sedation of Preschool Children Using Intranasal Midazolam", Anesthesiology, vol. 69, No. 6, Dec. 1988, pp. 972-975.
Chung Y.Lui et al., "Intranasal Absorption of Flurazepam, Midazolam, and Triazolam in Dogs", Journal of Pharmaceutical Sciences, vol. 80, No. 12, Dec. 1991, pp. 1125-1129.
Erik Bechgaard et al., "Pharmacokinetic and Pharmacodynamic Response after Intranasal Administration of Diazepam to Rabbits", J. Pharm. Pharmacol. 1997, 49; pp. 747-750.
S.W.J. Lau, et al., "Absorption of diazepam and lorazepam following intranasal administration", International Journal of Pharmaceutics, Elsevier Science Publishers B.V., 1989, 54, pp. 171-174.
S.H. Yalkowsky, et al., "Solubilization by Cosolvents I: Organic Solutes in Propylene Glycol-Water Mixtures", Journal of Pharmaceutical Sciences, vol. 74, No. 4, Apr. 1985, pp. 416-421.
Handbook of Pharmaceutical Excipients, Pharmaceutical Press, London and American Pharmacists Association, Washington, 2003, 4th Ed., 23 pages.
Bechgaard, Erik, et al. "Solubilization of Various Benzodiazepines for Intranasal Administration, a Pilot Study", Pharmaceutical Development and Technology, 2(3), 293-296 (1977).

(Continued)

*Primary Examiner* — Kara R McMillian
(74) *Attorney, Agent, or Firm* — Panitch Schwarze Belisario & Nadel LLP

(57) ABSTRACT

A composition for intranasal delivery of a drug comprising: includes: (i) the drug; and (ii) a non-aqueous vehicle containing (a) propylene glycol and at least one additional solvent selected from N-methylpyrrolidone, propylene carbonate, dimethyl sulfoxide and at least one propylene glycol fatty acid ester; (b) from about 40 to 100% by volume of N-methylpyrrolidone; or (c) from about 40 to 100% by volume of dimethyl sulfoxide (DMSO).

27 Claims, No Drawings

(56) References Cited

OTHER PUBLICATIONS

Nielsen, Hanne W. et al., "Solubilization and Stability of Bumetanide in Vehicles for Intranasal Administration, a Pilot Study"; Pharmaceutical Development and Technology, 6(2), 145-149 (2001).

Hjortkjaer, Rolf, et al., "Single-and Repeated-dose Local Toxicity in the Nasal Cavity of Rabbits after Intranasal Administration of Different Glycols for Formulations Containing Benzodiazepines"; J. Pharm. Pharmacol. 1999, 51:377-383.

Int'l Search Report and Written Opinion dated Feb. 11, 2010 in Int'l Application No. PCT/GB2008/002940, 21 pages.

Office Action dated Nov. 26, 2010 in NZ Patent Appln. No. 583265, 2 pages.

Handbook of Pharmaceutical Excipients, 6th Ed., Pharmaceutical Press, London—Chicago, pp. 517-591, 2009.

Notification of Grant issued May 3, 2012 in CN Application No. 200880114062.8.

Office Action issued Jun. 27, 2013 in AU Application No. 2008291873.

Office Action issued Aug. 1, 2013 in MX Application No. MX/a/2010/001911.

Office Action issued Apr. 30, 2013 in TW Application No. 97133070.

Office Action issued Jun. 11, 2013 in JP Application No. 2010-522446.

Office Action issued Nov. 12, 2013 in JP Application No. 2010-522446.

Notice of Acceptance issued Apr. 16, 2014 in Australian Application No. 2008291873.

Certificate of Patent for Japanese Patent No. 5539875 registered May 9, 2014.

Office Action issued Apr. 24, 2014 in EP Application No. 08 788 485.4.

Anonymous, "Handbook of Pharmaceutical Excipients," 5th edition (2006).

Office Action issued Feb. 7, 2014 in MX Application No. MX/a/2010/001911.

Office Action issued Feb. 13, 2014 in TW Applicaiton No. 097133070.

Notice of Allowance issued Apr. 7, 2014 in JP Application No. 2010-522446.

* cited by examiner

NON-AQUEOUS PHARMACEUTICAL COMPOSITION

BACKGROUND OF THE INVENTION

This invention relates to pharmaceutical compositions for the nasal administration of poorly water soluble drug compounds in which the drug is dissolved in a non-aqueous liquid vehicle.

The nasal route of drug delivery can afford rapid absorption of drugs into the blood circulation. In some cases absorption of almost the whole dose can be achieved and the pharmacokinetics can be similar to those achieved for intravenous administration. Such rapid and effective drug delivery can be useful in the treatment of crisis situations such as pain (including breakthrough pain and trauma pain), migraine, anxiety, convulsions, impotence and nausea.

Generally, it is preferable that compositions for the intranasal delivery of drugs are in the form of an aqueous solution. This is due to ease of manufacture, ease of delivery and good patient acceptability. However, it is not always feasible to formulate a drug as an aqueous solution, for example if the solubility of the drug in aqueous media is inadequate.

In such circumstances, one option would be to formulate the composition as a non-aqueous solution utilising solvents in which the drug has higher solubility. However, the nasal mucosal membrane is a delicate tissue and non-aqueous vehicles have a greater tendency to irritate the mucosa resulting in low acceptability to the patient. In this regard, the ideal vehicle will be odourless, tasteless and free from irritation when applied to the nasal cavity. Nasal solutions are typically delivered from spray devices that may comprise a range of glass, plastic, elastomeric and metal components. It is therefore essential that the vehicle does not interact with components of the spray device and impair the device performance, for example through sorption into plastic or elastomeric parts. It is also important that the characteristics of the liquid are such that it is atomised to form a dispersion of droplets when dispensed using a nasal spray device.

BRIEF SUMMARY OF THE INVENTION

It is an object of the present invention to provide a non-aqueous liquid vehicle that may be used as an alternative to an aqueous vehicle for intranasal drug delivery. Such non-aqueous vehicles may overcome solubility issues such as inadequate solubility that may occur in aqueous media and are suitable for intranasal delivery, e.g: they are typically substantially odourless and substantially tasteless and ideally free from irritation when applied to the nasal cavity.

The non-aqueous vehicles described in this application are suitable for producing compositions for the intranasal delivery of a wide range of drug compounds. It will be a straightforward matter for one skilled in the art to determine whether a particular non-aqueous vehicle is suitable for use in combination with a particular drug on the basis of the teaching in this application. For example, this can be done by measuring the solubility of the drug compound in the vehicle. The solubility can be tested by adding an excess of the drug to the vehicle and stirring the mixture for 24 hours at room temperature. Undissolved drug is then removed by filtration or centrifugation and the solution is assayed for dissolved drug content by an appropriate analytical method, such as high performance liquid chromatography.

Drugs suitable for use in this invention typically have a solubility in water at 20° C. of not more than about 1 mg/ml. Such drugs are often referred to in the literature as "very slightly soluble" (solubility in water at 20° C. of from 0.1 to 1 mg/ml) and "practically insoluble" or "insoluble" (for both, solubility in water at 20° C. of less than 0.1 mg/ml).

Therapeutic agents (drug compounds) suitable for use in this invention include, but are not limited to, antibiotics and antimicrobial agents, such as tetracycline hydrochloride, leucomycin, penicillin, penicillin derivatives, erythromycin, sulphathiazole and nitrofurazone; antimigraine compounds, such as naratriptan, sumatriptan, zolmitriptan, rizatriptan, eletriptan, frovatriptan, alnitidan, avitriptan, almotriptan or other 5-HT1 agonists; vasoconstrictors, such as phenylephedrine hydrochloride, tetrahydrozoline hydrochloride, naphazoline nitrate, oxymetazoline hydrochloride and tramazoline hydrochloride; cardiotonics, such as digitalis and digoxin; vasodilators, such as nitroglycerin and papaverine hydrochloride; bone metabolism controlling agents, such as vitamin D and active vitamin D3; sex hormones; hypotensives; anti-tumour agents; steroidal anti-inflammatory agents, such as hydrocortisone, prednisone, fluticasone, prednisolone, triamcinolone, triamcinolone acetonide, dexamethasone, betamethasone, beclomethasone and beclomethasone dipropionate; non-steroidal anti-inflammatory drugs, such as acetaminophen, aspirin, aminopyrine, phenylbutazone, mefenamic acid, ibuprofen, diclofenac sodium, aceclofenac, piroxicam, meloxicam, tenoxicam, ketoprofen, dexketoprofen, flurbiprofen, ibuprofen, indomethacin, colchicines and probenecid; enzymatic anti-inflammatory agents, such as chymotrypsin and bromelain seratiopeptidase; anti-histaminic agents, such as diphenhydramine hydrochloride, chlorpheniramine maleate and clemastine; anti-tussive expectorants, such as codeine phosphate and isoproterenol hydrochloride; analgesics such as opioids (like diamorphine, hydromorphone, buprenorphine, fentanyl, oxycodone, codeine, morphine and its polar metabolites, such as morphine-6-glucuronides and morphine-3-sulphate), or combinations of opioids and other analgesic agents such as non-steroidal anti-inflammatory drugs; anti-emetics, such as metoclopramide, ondansetron, granisetron, tropisetron, palonosetron, dolasetron, dronabinol and nabilone; drugs for treatment of sleeping disorders, such as melatonin, zolpidem, zaleplon and zopiclone; drugs for treatment of asthma, such as salbutamol; drugs for treatment of erectile dysfunction such as apomorphine, sildenafil, tadalafil, vardenafil and alprostadil; antipsychotic drugs such as haloperidol, olanzapine, risperidone, ziprasidone, clozapine, loxapine, pimozide, zotepine, quetiapine, flupentixol, zuclopenthixol and sertindole.

A further class of drug compounds of interest for nasal delivery is the benzodiazepines. These lipophilic drugs act on the central nervous system to cause sedation, hypnosis, decreased anxiety, muscle relaxation, anterograde amnesia and anticonvulsant actions and are widely used in medicine. Conditions which they can be used to treat include anxiety, epilepsy, insomnia, alcohol dependence, muscular disorders and mania. These drugs can also be used in premedication procedures and in veterinary practice. Examples of benzodiazepine drugs include, but are not limited to, alprazolam, chlordiazepoxide, clonazepam, clorazepate, diazepam, estazolam, flurazepam, halazepam, lorazepam, midazolam, nitrazepam, oxazepam, prazepam, quazepam, temazepam, bromazepam, flunitrazepam and triazolam, bentazepam, brotizolam, clotiazepam, delorazepam, ethyl loflazepate, etizolam, fludiazepam, ketozolam, loprazolam, lormetazepam, nordazepam, mexazolam, nimetazepam, pinazepam and tetrazepam. The structures of some of these benzodiazepines can be found in Goodman and Gilman's The Pharmacological Basis of Therapeutics, 9th edition, McGraw Hill (1996), page 383.

This invention can be applied to any of the classes of drugs and to the specific drugs listed above. In particular, the invention can be applied to any benzodiazepine compound, in particular any of the benzodiazepine drugs listed above. A preferred group of benzodiazepine drugs for use in this invention are diazepam (7-chloro-1,3-dihydro-1-methyl-5-phenyl-2H-1,4-benzodiazepin-2-one), lorazepam (7-chloro-5-(2-chlorophenyl)-1,3-dihydro-3-hydroxy-2H-1,4-benzodiazepin-2-one), clonazepam (5-(2-chlorophenyl)-1,3-dihydro-7-nitro-2H-1,4-benzodiazepin-2-one) and midazolam (8-chloro-6-(2-fluorophenyl)-1-methyl-4H-imidazo[1,5-a][1,4]benzodiazepine).

Lau and Slattery (Int. J. Pharm., 54, 171-174, 1989) investigated the intranasal delivery of diazepam and lorazepam using seven non-aqueous vehicles. These were triacetin, dimethyl sulfoxide, polyethylene glycol 400, Cremophor EL, laureth-9-(polyoxyethylene-9 lauryl ether), isopropyl adipate and azone 1-dodecylazacycloheptane-2-one.

U.S. Pat. No. 5,693,608 describes compositions for intranasal administration comprising an n-ethylene glycol (e.g. polyethylene glycol (PEG)). Examples are provided for diazepam, flunitrazepam and lorazepam dissolved in PEG 400 and flunitrazepam dissolved in a mixture of PEG 400 and glycofurol.

A lorazepam solution for intranasal administration using a solvent carrier comprising polyethylene glycol and propylene glycol is described in U.S. Pat. No. 6,610,271.

Supersaturated diazepam solutions are described in WO 2006/122217. Diazepam was dissolved in glycofurol to form a concentrated solution and water was added just prior to administration to form a supersaturated solution. It is claimed in this document that the water improves the nasal acceptability of the formulation. However, the need to add water prior to administration adds considerably to the dosing complexity.

The listing or discussion of an apparently prior-published document in this specification should not necessarily be taken as an acknowledgement that the document is part of the state of the art or is common general knowledge.

DETAILED DESCRIPTION OF THE INVENTION

The present inventors have surprisingly found that certain non-aqueous vehicles are suitable for use in compositions for the intranasal delivery of a variety of drug compounds.

The present invention provides compositions for intranasal delivery of a drug comprising (i) the drug, and (ii) a non-aqueous vehicle comprising (a) propylene glycol and at least one additional solvent selected from N-methylpyrrolidone, propylene carbonate, dimethyl sulfoxide and propylene glycol fatty acid esters, (b) from about 40 to 100% by volume of N-methylpyrrolidone, or (c) from about 40 to 100% by volume of dimethyl sulfoxide (DMSO). Unless otherwise stated, these compositions will be referred to hereinafter as the compositions of the invention and the non-aqueous vehicle will be referred to hereinafter as the vehicle of the invention.

The non-aqueous vehicle used in the invention is preferably a vehicle (a) consisting essentially of propylene glycol and at least one additional solvent selected from N-methylpyrrolidone, propylene carbonate, dimethyl sulfoxide and propylene glycol fatty acid esters, or (b) consisting essentially of from about 40 to 100% by volume of N-methylpyrrolidone, and an additional non-aqueous solvent or (c) consisting essentially of from about 40 to 100% by volume of dimethyl sulfoxide (DMSO), and an additional non-aqueous solvent.

The non-aqueous vehicle may be a vehicle (a) consisting of propylene glycol and at least one additional solvent selected from N-methylpyrrolidone, propylene carbonate, dimethyl sulfoxide and propylene glycol fatty acid esters, or (b) consisting of from about 40 to 100% by volume of N-methylpyrrolidone, and an additional non-aqueous solvent or (c) consisting of from about 40 to 100% by volume of dimethyl sulfoxide (DMSO), and an additional non-aqueous solvent.

For the avoidance of doubt, in this specification when we use the term "comprising" or "comprises" we mean that the composition or formulation or component being described must contain the listed ingredient(s) but may optionally contain additional ingredients. When we use the term "consisting essentially of" or "consists essentially of" we mean that the composition or formulation or component being described must contain the listed ingredient(s) and may also contain small (for example up to 5% by weight, or up to 1% or 0.1% by weight) of other ingredients provided that any additional ingredients do not affect the essential properties of the composition, formulation or component. When we use the term "consisting of" or "consists of" we mean that the composition or formulation or component being described must contain the listed ingredient(s) only.

Herein, when we refer to a component or ingredient in the singular, for example "a fatty acid ester" the phrase is also intended to cover the plural. For example "a fatty acid ester" can be considered to mean "at least one fatty acid ester".

The compositions of the invention may (i) be more stable than, (ii) be better tolerated than, (iii) be less toxic than, (iv) have better pharmacokinetic properties than, (v) be more easily prepared than, and/or (vi) have other useful properties over, compositions known in the prior art. In particular, the compositions of the invention may have one or more of the following advantages:

(a) they contain high concentrations of drug (e.g. higher concentrations than in equivalent prior art compositions);

(b) they can be atomised using a conventional intranasal spray device;

(c) they are well tolerated when applied into the nasal cavity;

(d) they provide a medium in which the drug is chemically stable; and/or (e) they provide for rapid and efficient intranasal absorption of the drug.

Compositions described herein as being "well tolerated" include those that cause little or no discomfort when applied into the nasal cavity. A "well tolerated" composition is also one that may cause some irritation and/or stinging when applied into the nasal cavity but it is such that the patient is not dissuaded from being administered further doses of the composition. In this respect, the tolerability of a nasal composition may be assessed by methods known to those skilled in the art, for example by use of a questionnaire, such as described in U.S. Pat. No. 5,693,608.

Compositions according to the invention that contain high concentrations of drug have the further advantage that a therapeutic dose of drug can be administered in a very small dose volume. This further improves patient acceptability and tolerance, since if a large volume of liquid is administered into the nasal cavity some of this may drip out of the nostrils. For example, if the dose of drug to be delivered is 5 mg, this will require a dose volume of 0.5 mL for a composition containing 10 mg/mL of the drug compound. If the drug content is increased to 50 mg/mL (for example by use of a composition according to the invention), the dose volume will be reduced to only 0.1 mL.

Moreover, compositions according to the invention also have the advantage that they may be prepared using established pharmaceutical processing methods and employ materials that are approved for use in food or pharmaceuticals or are of like regulatory status.

In one aspect, the invention provides a non-aqueous delivery vehicle comprising propylene glycol and at least one additional solvent selected from N-methylpyrrolidone (1-methyl-2-pyrrolidone), propylene carbonate (4-methyl-2-oxo-1,3-dioxolane), dimethyl sulfoxide and propylene glycol fatty acid ester(s). This vehicle will be referred to hereinafter as the "propylene glycol vehicle".

The use of a liquid vehicle comprising propylene glycol and an additional solvent selected from N-methylpyrrolidone, propylene carbonate, dimethyl sulfoxide and propylene glycol fatty acid ester(s) for intranasal delivery of drugs has not been described before. The use of this liquid vehicle will be discussed below with reference to use in combination with benzodiazepine drugs. However, this is by way of example only and this vehicle may also be used with other drugs such as those listed earlier in this text.

Propylene glycol (also known as 1,2-dihydroxypropane, 2-hydroxypropanol, methyl ethylene glycol, methyl glycol or propane-1,2-diol) is widely used as a solvent in parenteral and non-parenteral pharmaceutical formulations. It is well tolerated when applied to mucosal membranes. However, it is not a good solvent for all drugs and particularly not for all benzodiazepine drugs. Additionally, its viscosity and surface tension make it difficult to atomise effectively using conventional intranasal spray devices.

We have surprisingly found that mixtures of propylene glycol and other specific materials, particularly at least one material selected from N-methylpyrrolidone, propylene carbonate, dimethyl sulfoxide and propylene glycol fatty acid ester(s), enable stable solutions to be prepared containing high concentrations of drugs, such as benzodiazepines, and which can be successfully delivered using nasal spray devices. These vehicles comprise propylene glycol and one or more of N-methylpyrrolidone, propylene carbonate and a propylene glycol fatty acid ester.

The propylene glycol fatty acid esters used in the present invention may be mono or diesters of propylene glycol and have the basic structure

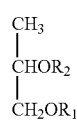

In the case of mono-esters one of $R_1$ and $R_2$ is hydrogen and the other is a fatty acid moiety. In the case of diesters $R_1$ and $R_2$ are both fatty acid moieties.

In the propylene glycol fatty acid esters used in the present invention, when $R_1$ and/or $R_2$ is a fatty acid moiety, they each individually have a carbon chain length which is primarily in the range of from C6 to C18. In other words, when $R_1$ and/or $R_2$ is a fatty acid moiety, the propylene glycol fatty acid ester typically is a mixture of esters with different chain lengths (such that primarily $R_1$ and/or $R_2$=C6 to C18 fatty acid moiety).

A single propylene glycol fatty acid ester may be used. Alternatively, a mixture of two or more propylene glycol fatty acid esters may be used.

An especially preferred propylene glycol fatty acid ester for use in this invention is a mono ester of medium chain fatty acids, primarily caprylic acid (C8).

By "primarily", we mean that at least 80% of the fatty acid content of the propylene glycol fatty acid ester is of the type specified.

A propylene glycol fatty acid ester comprising primarily the monoester of caprylic acid may be described as propylene glycol monocaprylate. Commercial suppliers of propylene glycol monocaprylate include Abitec Inc. (Columbus, Ohio USA) under the trade name Capmul® PG8 and Gattefosse (Saint Priest, France) under the trade names Capryol™ 90 and Capryol™ PGMC.

The propylene glycol vehicle of the present invention may comprise at least one additional solvent selected from N-methylpyrrolidone, propylene carbonate, dimethyl sulfoxide and propylene glycol fatty acid esters. Any combination may be used, for example each of these compounds may be used in a single vehicle. A single propylene glycol fatty acid ester may be used or a mixture of propylene glycol fatty acid esters may be used alone or in combination with N-methylpyrrolidone and/or propylene carbonate.

The propylene glycol vehicle typically comprises from about 10 to about 98% v/v of propylene glycol, or preferably from about 15 to about 95% v/v of propylene glycol and at least one additional solvent selected from N-methylpyrrolidone, propylene carbonate, dimethyl sulfoxide and propylene glycol fatty acid esters which alone or in combination typically comprise from about 2 to about 90% v/v, preferably from about 5 to about 85% v/v of the vehicle.

A particularly preferred combination for use in the present invention is propylene carbonate and a propylene glycol fatty acid ester, for example propylene carbonate and propylene glycol monocaprylate. It has surprisingly been found that the use of propylene carbonate and a propylene glycol fatty acid ester with propylene glycol has a cosolvent effect in that the solubility of a drug compound in a mixture comprising the two additional solvents is greater than the solubility in a solvent comprising one or other of them.

Examples of preferred vehicle compositions (% v/v) are provided in Table 1. The percentages represent the theoretical amount by volume in the final vehicle and do not take into account any non-additive volume changes when the individual components are mixed i.e. in the event that the mixture does not behave as an ideal solution. For example, a vehicle described as comprising 50% v/v propylene glycol and 50% v/v propylene carbonate may be prepared by mixing together 10 ml of each solvent (although the final volume may not necessarily be 20 ml). The composition of a vehicle may also be expressed in % w/w terms. For example, 10 ml of propylene glycol and 10 ml of propylene carbonate weigh approximately 10.37 g and 12.00 g respectively at room temperature. Hence, the final composition of this mixture will be 46% w/w propylene glycol and 54% w/w propylene carbonate.

As a further example, a vehicle comprising 50% w/w propylene glycol and 50% w/w N-methylpyrrolidone may be used to prepare a solution containing 10% w/w of drug compound. The final drug solution will contain 10% w/w drug, 45% w/w propylene glycol and 45% w/w N-methylpyrrolidone.

TABLE 1

Preferred nasal delivery vehicles

| | Composition (% v/v*) | | |
|---|---|---|---|
| | Preferred | More preferred | Most preferred |
| Composition A | | | |
| Propylene glycol | 20-95 | 25-90 | 30-85 |
| Propylene carbonate | 5-80 | 10-75 | 15-70 |
| Composition B | | | |
| Propylene glycol | 20-95 | 25-90 | 30-85 |
| Propylene glycol FAE** | 5-80 | 10-75 | 15-70 |
| Composition C | | | |
| Propylene glycol | 20-95 | 25-90 | 30-85 |
| N-methylpyrrolidone | 5-80 | 10-75 | 15-70 |
| Composition D | | | |
| Propylene glycol | 15-80 | 20-75 | 25-70 |
| Propylene glycol FAE | 6-65 | 9-60 | 12-55 |
| Propylene carbonate | 3-55 | 4-50 | 5-45 |
| Composition E | | | |
| Propylene glycol | 25-75 | 30-70 | 35-65 |
| Propylene glycol FAE | 10-50 | 15-45 | 20-40 |
| N-methylpyrrolidone | 20-40 | 15-35 | 10-30 |
| Composition F | | | |
| Propylene glycol | 30-70 | 35-65 | 40-60 |
| Propylene glycol FAE | 4-40 | 7-35 | 10-30 |
| Propylene carbonate | 4-40 | 7-35 | 10-30 |
| N-methylpyrrolidone | 1-24 | 3-21 | 5-18 |
| Composition G | | | |
| Propylene glycol | 10-60 | 15-50 | 20-40 |
| Dimethyl sulfoxide | 40-90 | 50-85 | 60-80 |

*Theoretical composition of vehicle assuming final volume is equal to sum of volume of individual components
**Propylene glycol fatty acid ester e.g. propylene glycol monocaprylate The amounts of propylene glycol fatty acid ester in this Table (and in Table 2) are the total amounts of that component, which may be made up with smaller amounts of two or more propylene glycol fatty acid esters.

The drug content of the final compositions, produced by dissolving the drug in the vehicle, is dependent primarily on the dose that needs to be delivered to the patient (i.e. the amount required to give a therapeutic effect), but is preferably from about 0.1 to about 2000 mg/ml, more preferably from about 0.5 to 1500 mg/ml and most preferably from about 1 to about 1000 mg/ml.

In addition to the drug, other ingredients may also be added to the non-aqueous vehicle. These additional ingredients include antioxidants, chelating agents, preservatives, flavourings, sweeteners or other agents generally used in pharmaceutical liquid preparations and are well known to those skilled in the art. In the context of this invention, these additional ingredients are not considered to be part of the vehicle.

Where the drug is a benzodiazepine, the composition preferably comprises from about 0.1 to 300 mg/ml, more preferably from about 0.5 to 250 mg/ml and most preferably from about 1 to about 200 mg/ml of the benzodiazepine. For example, the preferred midazolam concentration is from about 1 to about 100 mg/ml, the preferred clonazepam concentration is from about 0.5 to about 30 mg/ml and the preferred lorazepam concentration is from about 0.5 to about 50 mg/ml.

An especially preferred benzodiazepine compound is diazepam. The concentration of diazepam is preferably from about 1 to about 200 mg/ml, more preferably from about 2 to about 180 mg/ml and most preferably from about 5 to about 160 mg/ml, for example from about 10 to about 150 mg/ml or about 20 or about 50 to about 150 mg/ml.

The compositions of further preferred nasal delivery vehicles are shown in Table 2 below. These nasal delivery vehicles may be used, for example, when the drug is a benzodiazepine (e.g. diazepam). For the avoidance of doubt, however, it should be understood that the delivery vehicles of the invention may have a composition represented by a combination of the preferred, more preferred and most preferred values of the compositions set out in Table 1 and/or Table 2.

TABLE 2

Preferred nasal delivery vehicles

| | Composition (% v/v*) | | |
|---|---|---|---|
| | Preferred | More preferred | Most preferred |
| Composition I | | | |
| Propylene glycol | 30-90 | 40-85 | 45-80 |
| Propylene carbonate | 10-70 | 15-60 | 20-55 |
| Composition II | | | |
| Propylene glycol | 35-90 | 45-85 | 50-80 |
| N-methylpyrrolidone | 10-65 | 15-55 | 20-50 |
| Composition III | | | |
| Propylene glycol | 20-75 | 25-70 | 30-65 |
| Propylene glycol FAE** | 9-60 | 12-65 | 15-50 |
| Propylene carbonate | 3-50 | 5-45 | 7-40 |
| Composition IV | | | |
| Propylene glycol | 30-70 | 35-65 | 40-60 |
| Propylene glycol FAE | 15-45 | 20-40 | 25-35 |
| N-methylpyrrolidone | 9-31 | 12-28 | 15-25 |
| Composition V | | | |
| Propylene glycol | 35-65 | 40-60 | 45-55 |
| Propylene glycol FAE | 9-31 | 12-28 | 15-25 |
| Propylene carbonate | 9-31 | 12-28 | 15-25 |
| N-methylpyrrolidone | 3-21 | 5-18 | 7-15 |
| Composition VI | | | |
| Propylene glycol | 10-60 | 15-50 | 20-40 |
| Dimethyl sulfoxide | 40-90 | 50-85 | 60-80 |

*Theoretical composition of vehicle assuming final volume is equal to sum of volume of individual components
**Propylene glycol fatty acid ester e.g. propylene glycol monocaprylate A particularly preferred vehicle for use in the present invention is a 1:1:1 (by volume) mixture of propylene glycol, propylene carbonate and propylene glycol fatty acid ester. This vehicle is particularly suitable for use with a benzodiazepine drug but may also be used with other drugs. A preferred composition of the invention comprises this vehicle and diazepam in a concentration of from 80 to 120 mg/ml. Other preferred vehicles are a 3:1 (by volume) mixture of propylene glycol and propylene carbonate and a 4:1 (by volume) mixture of DMSO and propylene glycol. Other preferred compositions of the invention comprise one of these vehicles and a benzodiazepine, for example diazepam in a concentration of from 80 to 120 mg/ml although these vehicles may also be used with other drugs.

One preferred diazepam composition comprises from about 10 to about 80 mg/ml diazepam dissolved in a vehicle comprising from about 50 to about 80% by volume propylene glycol and from about 20 to about 50% by volume propylene carbonate.

A second preferred diazepam composition comprises from about 10 to about 100 mg/ml diazepam dissolved in a vehicle comprising from about 30 to about 35% by volume propylene glycol, from about 30 to about 35% by volume propylene carbonate and from about 30 to about 35% by volume propylene glycol monocaprylate.

In another aspect, the invention provides for the use of high concentrations of N-methylpyrrolidone as a non-aqueous vehicle for intranasal drug delivery. By high concentration, we mean that the N-methylpyrrolidone content of the vehicle in which the drug is dissolved is from about 40 to 100% by volume, more preferably from about 45 to 100% and most preferably from about 50 to 100%. The remainder of the vehicle will comprise other pharmaceutically-acceptable solvents (alone or in combination). This vehicle is referred to hereinafter as the "N-methylpyrrolidone vehicle".

Examples of pharmaceutically-acceptable solvents that may be used in combination with N-methylpyrrolidone may be found in reference books such as the Handbook of Pharmaceutical Excipients (Fifth Edition, Pharmaceutical Press, London and American Pharmacists Association, Washington, 2006) and include, but are not limited to, propylene glycol, propylene carbonate, polyethylene glycol, ethanol, glycerol, glycofurol and propylene glycol fatty acid esters. These solvents individually or in mixture/combination may be used with the N-methyl pyrrolidone to make up the non-aqueous vehicle. The non-aqueous vehicle comprises from 0 to 60% preferably from 0 to 55% or from 0 to 50% by volume of the or each pharmaceutically acceptable solvent that is not N-methyl-pyrollidone, provided that the total amount of non-N-methylpyrrolidone solvent does not exceed 60%, preferably 55% or 50% of the total volume of the vehicle. The vehicle may consist essentially of or consist of N-methylpyrrolidone and optionally these non-aqueous solvents. However, a suitable composition may comprise a drug and N-methylpyrrolidone only, with no other ingredients added.

The use of this liquid vehicle will be discussed below with reference to use in combination with benzodiazepine drugs. However, this is by way of example only and this vehicle may also be used with other drugs such as those listed earlier in this text.

In a particular aspect, the present invention provides compositions suitable for intranasal delivery which comprise the N-methylpyrrolidone vehicle and a benzodiazepine, such as those listed earlier herein, for example diazepam, lorazepam, clonazepam or midazolam.

The compositions comprising the N-methylpyrrolidone vehicle may be prepared by dissolving the drug in the vehicle. The compositions comprising the N-methylpyrrolidone vehicle preferably comprise from about 0.1 to about 2000 mg/ml, more preferably from about 0.5 to about 1500 mg/ml and most preferably from about 1 to about 1000 mg/ml of the drug.

If the drug is a benzodiazepine, the compositions comprising the N-methylpyrrolidone vehicle preferably comprise from about 0.1 to about 1000 mg/ml, more preferably from about 0.5 to about 800 mg/ml and most preferably from about 1 to about 600 mg/ml of the drug. For example, the preferred midazolam concentration from about 1 to about 400 mg/ml, the preferred clonazepam concentration is from about 0.5 to about 100 mg/ml and the preferred lorazepam concentration is from about 0.5 to about 200 mg/ml.

In addition to the drug, other ingredients may also be added to the non-aqueous vehicle. These additional ingredients include antioxidants, chelating agents, preservatives, flavourings, sweeteners or other agents generally used in pharmaceutical liquid preparations and are well known to those skilled in the art. In the context of this invention, these additional ingredients are not considered to be part of the vehicle.

In another aspect, the invention provides for the use of high concentrations of dimethyl sulfoxide (DMSO) as non-aqueous vehicles for intranasal drug delivery. Dimethyl sulfoxide has an established pharmaceutical use in injectable and topical formulations. The vehicle may comprise only dimethyl sulfoxide. However, one of the potential limitations to the use of high concentrations of dimethyl sulfoxide is its relatively high melting point (18.3° C.) which means pharmaceutical compositions at room temperature (typically 15-25° C.) could be in a semi-solid form. We have established that mixtures of dimethyl sulfoxide and certain other non-aqueous liquids are suitable for dissolving high concentrations of drugs and the mixtures stay liquid at room temperature.

By high concentration, we mean that the dimethyl sulfoxide content of the vehicle in which the drug is dissolved is from about 40 to 100% by volume, more preferably from about 45 to 95% and most preferably from about 50 to 90%. The vehicle preferably contains up to 90% DMSO, more preferably up to 85% DMSO and most preferably up to 80% DMSO by volume. The remainder of the vehicle will comprise other pharmaceutically-acceptable solvents (alone or in combination). These vehicles are referred to hereinafter as the "dimethyl sulfoxide vehicle".

Examples of pharmaceutically-acceptable solvents that may be used in combination with dimethyl sulfoxide may be found in reference books such as the Handbook of Pharmaceutical Excipients (Fifth Edition, Pharmaceutical Press, London and American Pharmacists Association, Washington, 2006) and include, but are not limited to, propylene glycol, propylene carbonate, polyethylene glycol, ethanol, glycerol, glycofurol and propylene glycol fatty acid esters. These solvents may be used alone or in mixture together with dimethyl sulfoxide to provide the dimethyl sulfoxide vehicle of the invention. Such a vehicle comprises from 0 to 60%, preferably from 5 to 55% or from 10 to 50% by volume of the or each pharmaceutically acceptable solvent that is not DMSO, provided that the total amount of non-DMSO solvent does not exceed 60%, preferably 55% or 50% of the total volume of the vehicle. The vehicle may consist essentially of or consist of DMSO and optionally one or more of these non-aqueous solvents. A preferred solvent for combining with dimethyl sulfoxide is propylene glycol.

The use of this liquid vehicle will be discussed below with reference to use in combination with benzodiazepine drugs. However, this is by way of example only and this vehicle may also be used with other drugs such as those listed earlier in this text.

In a particular aspect, the present invention provides compositions suitable for intranasal delivery which comprise the dimethyl sulfoxide vehicle and a benzodiazepine, such as those listed earlier herein, for example diazepam, lorazepam, clonazepam or midazolam.

The compositions comprising the dimethyl sulfoxide vehicle may be prepared by dissolving the drug in the vehicle. The compositions comprising the dimethyl sulfoxide vehicle preferably comprise from about 0.1 to about 2000 mg/ml, more preferably from about 0.5 to about 1500 mg/ml and most preferably from about 1 to about 1000 mg/ml of the drug.

If the drug is a benzodiazepine, the compositions comprising the dimethyl sulfoxide vehicle preferably comprise from about 0.1 to about 1000 mg/ml, more preferably from about 0.5 to about 800 mg/ml and most preferably from about 1 to about 600 mg/ml of the drug. For example, the preferred midazolam concentration from about 1 to about 400 mg/ml, the preferred clonazepam concentration is from about 0.5 to about 100 mg/ml and the preferred lorazepam concentration is from about 0.5 to about 200 mg/ml.

A particularly preferred composition of the invention comprises the N-methyl pyrrolidone vehicle or dimethyl sulfoxide vehicle and diazepam. In this composition, the concentration of diazepam is preferably from about 1 to about 1000 mg/ml, more preferably from about 5 to about 800 mg/ml and most preferably from about 10 or 20 to about 600 mg/ml, for example up to about 100 mg/ml, for example about 50 mg/ml.

A preferred vehicle comprises from about 60 to about 85 or 80% by volume DMSO and from about 15 or 20 to about 40% by volume propylene glycol, for example about 75% to about 85% by volume dimethyl sulfoxide and about 15 to 25% by volume propylene glycol. A preferred drug for including in this vehicle is diazepam, at a concentration of up to about 100 mg/ml, for example up to about 60 mg/ml, e.g. about 50 mg/ml.

In addition to the drug, other ingredients may also be added to the non-aqueous vehicle. These additional ingredients include antioxidants, chelating agents, preservatives, flavourings, sweeteners or other agents generally used in pharmaceutical liquid preparations and are well known to those skilled in the art. In the context of this invention, these additional ingredients are not considered to be part of the vehicle.

It has surprisingly been found that the DMSO containing vehicles of the present invention provide compositions in which they are used with especially good spray characteristics, often comparable to those achieved with aqueous solutions.

It is preferred that the compositions of the invention do not comprise triglyceride or an organic acid, organic acid ester or organic acid ether (such as citric acid or its ester or ether). It is typically not necessary for the compositions of the invention to include a permeabilizing agent. Thus in a preferred aspect the compositions of the invention do not comprise peptide permeabilizing agents such as those described in US 2004/0077540.

In another aspect of the invention, the non-aqueous vehicle does not comprise an alkoxy-polyethylene glycol such as methoxy-polyethylene glycol, more particularly, the compositions of the invention preferably do not comprise alkoxy-polyethylene glycol such as methoxy-polyethylene glycol.

In another aspect of the invention, the non-aqueous vehicle does not comprise an ethyl ether solvent such as diethylene glycol monoethylether or tetrahydrofurfuryl alcohol polyethyleneglycol ether, more particularly, the compositions of the invention preferably do not comprise an ethyl ether solvent such as diethylene glycol monoethylether or tetrahydrofurfuryl alcohol polyethyleneglycol ether.

The compositions of the invention preferably have a viscosity, measured by apparatus such as a cone and plate viscometer, of less than about 100 cP (mPas), more preferably less than 60 cP and most preferably less than 30 cP.

There are a number of different methods by which the drug formulations described in this application can be produced. For example, in one method the non-aqueous vehicle is first prepared by mixing together the vehicle components in the required quantities by volume or by weight. The required amount of drug and any other ingredients such as stabilisers or flavourings may then be weighed into a suitable vessel, a portion of the vehicle added (e.g. 90% of final amount) and the mixture stirred until the drug is dissolved. The drug solution is then made up to the required weight or volume by adding more of the drug to the non-aqueous vehicle. In another method, the drug (and any other ingredients if appropriate) is weighed into a suitable vessel and the exact weight of each solvent added. The mixture is then stirred until drug is dissolved. Following either of these methods, the final drug solution may be filtered if necessary.

Solutions comprising a vehicle of the invention and a drug may be administered to the nasal cavity in any suitable form for example in the form of drops or as a spray. The preferred method of administration is as a spray, e.g. using a spray device. Spray devices can be single ("unit") dose or multiple dose systems, for example comprising a bottle, pump and actuator, and are available from various commercial sources, including Pfeiffer (Germany), Valois (France), Rexam (France) and Becton-Dickinson (USA).

The present invention provides a nasal drug delivery device or a dose cartridge for use in a nasal delivery device loaded with a composition of the invention.

Nasal spray devices of the types described above typically dispense between 0.04 and 0.25 ml in a single actuation.

Typical nasal dosing regimens range from a single spray into one nostril to up to two sprays into each nostril.

The total liquid volume of solution delivered into the nasal cavity, using one or both nostrils in order to deliver the therapeutic dose of drug using the compositions of this invention is preferably from about 0.005 to about 1.0 ml, more preferably from about 0.01 to about 0.8 ml and most preferably from about 0.02 to about 0.6 ml, for example from about 0.1 to about 0.4 ml.

The present invention provides the use of a vehicle of the invention as described above in the manufacture of a medicament for the intranasal delivery of a drug to a patient in need of that drug.

The present invention provides compositions for use in the nasal delivery of a drug to a patient in need of that drug which compositions comprise a vehicle of the invention as described above and the drug.

The present invention provides processes for preparing the compositions of the invention. These processes are as described above.

The compositions of the invention comprising a benzodiazepine, such as those mentioned above, can be used to treat and/or prevent certain disorders, conditions or diseases of the central nervous system and in particular can be used to cause sedation, hypnosis, decreased anxiety, muscle relaxation, anterograde amnesia and anticonvulsant actions. They can also be used to treat anxiety, epilepsy, insomnia, alcohol dependence, muscular disorders and mania. Thus, the present invention provides a method of administering a benzodiazepine drug compound, particularly a compound as listed above, to a patient in need thereof, for example for the prevention and/or treatment of the disorders, conditions or diseases set out above and/or to induce the effects set out above, which comprises the intranasal administration of a composition of the invention.

As used herein, we use the term patient to refer to both human and non-human animals. The invention is particularly suitable for use in the treatment of humans and animals such as dogs, horses, sheep, cattle, pigs and other larger mammals.

The present invention also provides the use of a vehicle of the invention as described above and a benzodiazepine drug, such as a drug as listed above, in the manufacture of a medicament for nasal administration to a patient in need thereof. Such a medicament may be for the treatment and/or prevention of disorders, conditions or diseases of the central nervous system and/or to induce sedation, hypnosis, decreased anxiety, muscle relaxation, anterograde amnesia and anticonvulsant actions or treat anxiety, epilepsy, insomnia, alcohol dependence, muscular disorders and mania.

The present invention also provides compositions comprising a vehicle of the invention as described above and a benzodiazepine drug compound and optionally additional ingredients as defined above for use in nasal delivery for treating disorders, conditions or diseases of the central nervous system and/or to induce sedation, hypnosis, decreased anxiety, muscle relaxation, anterograde amnesia and anticonvulsant actions or treat anxiety, epilepsy, insomnia, alcohol dependence, muscular disorders and mania.

The compositions of the invention may comprise an anti-emetic drug, such as those mentioned above. These compositions can be used to treat and/or prevent nausea and vomiting. Thus, the present invention provides a method of administering an anti-emetic drug compound, particularly a compound as listed above, to a patient in need thereof, which comprises the intranasal administration of a composition of the invention.

The present invention also provides the use of a vehicle of the invention as described above and an anti-emetic drug, such as a drug as listed above, in the manufacture of a medicament for nasal administration to a patient in need thereof. Such a medicament may be used for the treatment and/or prevention of nausea and vomiting.

The present invention also provides compositions comprising a vehicle of the invention as described above and an anti-emetic drug compound and optionally additional ingredients as defined above for use in nasal delivery. Such compositions may be used to treat and/or prevent nausea and vomiting.

The compositions of the invention may comprise an anti-psychotic drug, such as those mentioned above. These compositions can be used to treat psychoses such as schizophrenia or mania. Thus, the present invention provides a method of administering an anti-psychotic drug compound, particularly a compound as listed above, to a patient in need thereof, which comprises the intranasal administration of a composition of the invention.

The present invention also provides the use of a vehicle of the invention as described above and an anti-psychotic drug, such as a drug as listed above, in the manufacture of a medicament for nasal administration to a patient in need thereof. Such a medicament may be used for the treatment and/or prevention of psychoses such as schizophrenia or mania.

The present invention also provides compositions comprising a vehicle of the invention as described above and an anti-psychotic drug compound and optionally additional ingredients as defined above for use in nasal delivery. Such compositions may be used to treat and/or prevent psychoses such as schizophrenia or mania.

The compositions of the invention may comprise an anti-migraine drug, such as those mentioned above. These compositions can be used to treat and/or prevent migraine. Thus, the present invention provides a method of administering an anti-migraine drug compound, particularly a compound as listed above, to a patient in need thereof, which comprises the intranasal administration of a composition of the invention.

The present invention also provides the use of a vehicle of the invention as described above and an anti-migraine drug, such as a drug as listed above, in the manufacture of a medicament for nasal administration to a patient in need thereof. Such a medicament may be used for the treatment and/or prevention of migraine.

The present invention also provides compositions comprising a vehicle of the invention as described above and an anti-migraine drug compound and optionally additional ingredients as defined above for use in nasal delivery. Such compositions may be used to treat and/or prevent migraine.

The compositions of the invention may comprise a drug for treating sleeping disorders, such as those mentioned above. These compositions can be used to treat and/or prevent sleeping disorders. Thus, the present invention provides a method of administering a drug compound for treating sleeping disorders, particularly a compound as listed above, to a patient in need thereof, which comprises the intranasal administration of a composition of the invention.

The present invention also provides the use of a vehicle of the invention as described above and a drug for treating sleeping disorders, such as a drug as listed above, in the manufacture of a medicament for nasal administration to a patient in need thereof. Such a medicament may be used for the treatment and/or prevention of sleeping disorders.

The present invention also provides compositions comprising a vehicle of the invention as described above and a drug compound for treating sleeping disorders and optionally additional ingredients as defined above for use in nasal delivery. Such compositions may be used to treat and/or prevent sleeping disorders.

The compositions of the invention may comprise a drug for treating erectile dysfunction, such as those mentioned above. These compositions can be used to treat and/or prevent erectile dysfunction. Thus, the present invention provides a method of administering a drug compound for erectile dysfunction, particularly a compound as listed above, to a patient in need thereof, which comprises the intranasal administration of a composition of the invention.

The present invention also provides the use of a vehicle of the invention as described above and a drug for treating erectile dysfunction, such as a drug as listed above, in the manufacture of a medicament for nasal administration to a patient in need thereof. Such a medicament may be used for the treatment and/or prevention of erectile dysfunction.

The present invention also provides compositions comprising a vehicle of the invention as described above and a drug compound for treating erectile dysfunction and optionally additional ingredients as defined above for use in nasal delivery. Such compositions may be used to treat and/or prevent erectile dysfunction.

The invention is illustrated by the following non-limiting Examples.

Example 1

Solution Containing 50 mg/ml Diazepam in Propylene Glycol/Propylene Carbonate (3:1)

The non-aqueous vehicle was prepared by mixing together 16.5 ml of propylene glycol (Sigma, Poole, UK) and 5.5 ml of propylene carbonate (Lyondell Chemical Co, USA) in a glass vial. 1 g of diazepam (Cambrex, Italy) was weighed into a 20 ml volumetric flask and 18 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 2

Solution Containing 50 mg/ml Diazepam in Propylene Glycol/Propylene Glycol Monocaprylate/Propylene Carbonate (5:4:1)

The non-aqueous vehicle was prepared by mixing together 11 ml of propylene glycol, 8.8 ml of propylene glycol monocaprylate (Capmul® PG-8, Abitec, USA) and 2.2 ml of propylene carbonate in a glass vial. 1 g of diazepam was weighed into a 20 ml volumetric flask and 18 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 3

Solution Containing 50 mg/ml Diazepam in Propylene Glycol/Propylene Glycol Monocaprylate/Propylene Carbonate (6:3:1)

The non-aqueous vehicle was prepared by mixing together 13.2 ml of propylene glycol, 6.6 ml of propylene glycol monocaprylate and 2.2 ml of propylene carbonate in a glass vial. 1 g of diazepam was weighed into a 20 ml volumetric flask and 18 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 4

Solution Containing 50 mg/ml Diazepam in Propylene Glycol/Propylene Glycol Monocaprylate/Propylene Carbonate (4.5:4.5:1)

The non-aqueous vehicle was prepared by mixing together 9.9 ml of propylene glycol, 9.9 ml of propylene glycol monocaprylate and 2.2 ml of propylene carbonate in a glass vial. 1 g of diazepam was weighed into a 20 ml volumetric flask and 18 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 5

Solution Containing 50 mg/ml Diazepam in Propylene Glycol/Propylene Glycol Monocaprylate/N-Methylpyrrolidone (5:3:2)

The non-aqueous vehicle was prepared by mixing together 11.0 ml of propylene glycol, 6.6 ml of propylene glycol monocaprylate and 4.4 ml of N-methylpyrrolidone (Sigma) in a glass vial. 1 g of diazepam was weighed into a 20 ml volumetric flask and 18 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 6

Solution Containing 50 mg/ml Diazepam in Propylene Glycol/Propylene Glycol Monocaprylate/Propylene Carbonate (6:2:2)

The non-aqueous vehicle was prepared by mixing together 9.9 ml of propylene glycol, 9.9 ml of propylene glycol monocaprylate and 2.2 ml of propylene carbonate in a glass vial. 1 g of diazepam was weighed into a 20 ml volumetric flask and 18 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 7

Solution Containing 75 mg/ml Diazepam in Propylene Glycol/Propylene Glycol Monocaprylate/Propylene Carbonate (5:3.5:1.5)

The non-aqueous vehicle was prepared by mixing together 11 ml of propylene glycol, 7.7 ml of propylene glycol monocaprylate and 3.3 ml of propylene carbonate in a glass vial. 1.5 g of diazepam was weighed into a 20 ml volumetric flask and 18 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 8

Solution Containing 75 mg/ml Diazepam in Propylene Glycol/Propylene Carbonate (1:1)

The non-aqueous vehicle was prepared by mixing together 11 ml of propylene glycol and 11 ml of propylene carbonate in a glass vial. 1.5 g of diazepam was weighed into a 20 ml volumetric flask and 18 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 9

Solution Containing 75 mg/ml Diazepam in Propylene Glycol/Propylene Glycol Monocaprylate/N-Methylpyrrolidone/Propylene Carbonate (5:2:1:2)

The non-aqueous vehicle was prepared by mixing together 11 ml of propylene glycol, 4.4 ml of propylene glycol monocaprylate, 4.4 ml of propylene carbonate and 2.2 ml of N-methylpyrrolidone in a glass vial. 1.5 g of diazepam was weighed into a 20 ml volumetric flask and 18 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 10

Solution Containing 125 mg/ml Diazepam in Propylene Glycol/Propylene Glycol Monocaprylate/Propylene Carbonate (1:1:1)

The non-aqueous vehicle was prepared by mixing together 7.33 ml of propylene glycol, 7.33 ml of propylene glycol monocaprylate and 7.33 ml of propylene carbonate in a glass vial. 1.5 g of diazepam was weighed into a 20 ml volumetric flask and 18 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 11

Solution Containing 20 mg/ml Midazolam in Propylene Glycol/Propylene Glycol Monocaprylate/Propylene Carbonate (2:1:1)

The non-aqueous vehicle was prepared by mixing together 4 ml of propylene glycol, 2 ml of propylene glycol monocaprylate and 2 ml of propylene carbonate in a glass vial. 100 mg of midazolam (Sifa, Ireland) was weighed into a 5 ml volumetric flask and 4 ml of the non-aqueous vehicle was added. The flask contents were stirred until the drug had dissolved and the solution was made up to volume with the non-aqueous vehicle.

Example 12

Solution Containing 10 mg/ml Lorazepam in Propylene Glycol/Propylene Glycol Monocaprylate/Propylene Carbonate (3:1:1)

The non-aqueous vehicle was prepared by mixing together 3 ml of propylene glycol, 1 ml of propylene glycol monocaprylate and 1 ml of propylene carbonate in a glass vial. 20 mg of lorazepam (Sigma) was weighed into a second glass vial and 2 ml of the non-aqueous vehicle added. The vial contents were stirred until the drug had dissolved.

Example 13

Solution Containing 10 mg/ml Lorazepam in Propylene Glycol/N-Methylpyrrolidone (1:1)

The non-aqueous vehicle was prepared by mixing together 3 ml of propylene glycol and 3 ml of N-methylpyrrolidone in a glass vial. 20 mg of lorazepam (Sigma) was weighed into a second glass vial and 2 ml of the non-aqueous vehicle added. The vial contents were stirred until the drug had dissolved.

Example 14

Solution Containing 200 mg/ml Diazepam in N-Methylpyrrolidone 1 gram of diazepam was weighed into a volumetric flask. Approximately 4 ml of N-methylpyrrolidone was added and the flask contents stirred until the drug was dissolved. The flask contents were then made up to volume with N-methylpyrrolidone.

Example 15

Solution Containing 50 mg/ml Diazepam in Propylene Glycol/Dimethyl Sulfoxide (1:3)

The non-aqueous vehicle was prepared by mixing together 1.25 ml of propylene glycol and 3.75 ml of dimethyl sulfoxide in a glass vial. 100 mg of diazepam was weighed into a 2 ml volumetric flask and 1.5 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 16

Solution Containing 50 mg/ml Diazepam in Propylene Glycol/Dimethyl Sulfoxide (1:4)

The non-aqueous vehicle was prepared by mixing together 1 ml of propylene glycol and 4 ml of dimethyl sulfoxide in a glass vial. 100 mg of diazepam was weighed into a 2 ml volumetric flask and 1.5 ml of the non-aqueous vehicle added. The flask contents were mixed using a magnetic stirrer and stirrer bar. When the drug had dissolved the stirrer bar was removed and the flask contents made up to volume using the non-aqueous vehicle.

Example 17

Single Dose Nasal Spray Delivering 5 Mg of Diazepam

The solution prepared in Example 1 was dispensed into the glass vial of a Pfeiffer (Radolfzell, Germany) unit dose spray device. The vial was sealed with an elastomer closure, placed into the vial holder and the vial holder snapped into place onto the actuator piece of the spray device. On actuation, the device dispensed 0.1 ml of liquid as a spray plume containing 5 mg of diazepam.

Example 18

Multiple Dose Nasal Spray Delivering 5 Mg of Diazepam 1.5 ml of the solution prepared in Example 1 was dispensed into a 5 ml glass vial (Adelphi, UK). A Pfeiffer nasal spray pump (0.1 ml spray volume) was snapped onto the vial. The spray pump was primed by actuating four times. Each actuation of the primed pump dispensed 0.1 ml of liquid as a spray plume and containing 5 mg of diazepam.

Example 19

Nasal Spray Delivering 10 Mg of Diazepam 0.24 ml of the solution in Example 1 was filled into an Accuspray nasal drug delivery system (BD, Grenoble, France), which comprises a 0.5 ml pre-filled syringe fitted with a nasal atomiser. A 0.1 ml dose divider clip was attached to the plunger arm of the Accuspray system. On actuation, the dose divider allowed 0.1 ml of liquid to be dispensed in the form of a spray, equivalent to 5 mg diazepam. On removal of the dose divider clip, the remainder of the drug solution (excluding 0.04 ml overage) was delivered (further 5 mg of diazepam).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. A non-aqueous liquid composition for intranasal delivery of a benzodiazepine drug consisting essentially of:
 (i) the drug; and
 (ii) a non-aqueous vehicle consisting essentially of about 30 to 85% v/v propylene glycol and 15 to 70% v/v propylene carbonate,
 wherein the non-aqueous liquid composition is suitable for delivery in a form of drops or a spray.
2. A composition according to claim 1, wherein the drug is selected from alprazolam, chlordiazepoxide, clonazepam, clorazepate, diazepam, estazolam, flurazepam, halazepam, lorazepam, midazolam, nitrazepam, oxazepam, prazepam, quazepam, temazepam, bromazepam, flunitrazepam, triazolam, bentazepam, brotizolam, clotiazepam, delorazepam, ethyl loflazepate, etizolam, fludiazepam, ketozolam, lopra- zolam, lormetazepam, nordazepam, mexazolam, nimetazepam, pinazepam and tetrazepam.

3. A composition according to claim 2, wherein the drug is diazepam, lorazepam, clonazepam or midazolam.

4. A method for intranasal delivery of a benzodiazepine drug to a patient in need thereof, the method comprising providing a non-aqueous liquid composition consisting essentially of a benzodiazepine drug and a non-aqueous vehicle for the drug, the vehicle consisting essentially of about 30 to 85% v/v propylene glycol and 15 to 70% v/v propylene carbonate; and intranasally administering the non-aqueous liquid composition to the patient in a form of drops or a spray.

5. A method according to claim 4, wherein the drug is selected from alprazolam, chlordiazepoxide, clonazepam, clorazepate, diazepam, estazolam, flurazepam, halazepam, lorazepam, midazolam, nitrazepam, oxazepam, prazepam, quazepam, temazepem, bromazepam, flunitrazepam, triazolam, bentazepam, brotizolam, clotiazepam, delorazepam, ethyl loflazepate, etizolam, fludiazepam, ketozolam, loprazolam, lormetazepam, nordazepam, mexazolam, nimetazepam, pinazepam and tetrazepam.

6. A method according to claim 5, wherein the drug is diazepam, lorazepam, clonazepam or midazolam.

7. A composition according to claim 1, wherein the non-aqueous vehicle consists essentially of 45 to about 80% v/v propylene glycol and about 20 to 55% v/v propylene carbonate.

8. A composition according to claim 1, consisting essentially of:
   (i) about 10 to about 80 mg/mL diazepam; and
   (ii) a non-aqueous vehicle consisting essentially of about 50 to about 80% by volume propylene glycol and about 20 to about 50% by volume propylene carbonate.

9. A composition according to claim 3, wherein the drug is diazepam.

10. A method according to claim 6, wherein the drug is diazepam.

11. A composition according to claim 8, wherein the non-aqueous vehicle consists essentially of about 50% to 75% v/v propylene glycol and 25% to about 50% v/v propylene carbonate.

12. A composition according to claim 1, wherein the drug consists of diazepam and the non-aqueous vehicle consists of propylene glycol and propylene carbonate.

13. A composition according to claim 12, wherein the non-aqueous vehicle consists of 45% to about 80% v/v propylene glycol and about 20% to 55% v/v propylene carbonate.

14. A composition according to claim 13, wherein the drug consists of about 10 to about 80 mg/mL diazepam; and the non-aqueous vehicle consists of about 50% to 75% v/v propylene glycol and 25% to about 50% v/v propylene carbonate.

15. A composition according to claim 1 having a viscosity of less than about 100 cP.

16. A composition according to claim 15 having a viscosity of less than 60 cP.

17. A composition according to claim 16 having a viscosity of less than 30 cP.

18. A method according to claim 4, wherein the non-aqueous liquid composition has a viscosity of less than about 100 cP.

19. A method according to claim 18, wherein the non-aqueous liquid composition has a viscosity of less than 60 cP.

20. A method according to claim 19, wherein the non-aqueous liquid composition has a viscosity of less than 30 cP.

21. A method for treating anxiety or epilepsy or for inducing sedation or anticonvulsant actions, the method comprising providing a non-aqueous liquid composition consisting essentially of a benzodiazepine drug selected from diazepam, lorazepam, clonazepam and midazolam in an amount effective for treating anxiety or epilepsy or for inducing sedation or anticonvulsant actions, and a non-aqueous vehicle consisting essentially of about 30 to 85% v/v propylene glycol and 15 to 70% v/v propylene carbonate; and intranasally administering the non-aqueous liquid composition to the patient in a form of drops or a spray.

22. A method according to claim 21 for treating epilepsy.

23. A method according to claim 21 for inducing anticonvulsant actions.

24. A method according to claim 21, wherein the benzodiazepine drug is diazepam or midazolam.

25. A method according to claim 24, wherein the benzodiazepine drug is diazepam.

26. A method according to claim 25 for treating epilepsy.

27. A method according to claim 25 for inducing anticonvulsant actions.

* * * * *